United States Patent [19]
Ohki et al.

[11] Patent Number: 5,647,349
[45] Date of Patent: Jul. 15, 1997

[54] MEDICINE ADMINISTERING INHALING DEVICE

[75] Inventors: Hisatomo Ohki; Shigemi Nakamura, both of Isesaki; Kazunori Ishizeki, Fujimi; Akira Yanagawa, Yokohama, all of Japan

[73] Assignees: Unisia Jecs Corporation, Atsugi; Dott Limited Company, Yokohama, both of Japan

[21] Appl. No.: 655,866

[22] Filed: May 31, 1996

[30] Foreign Application Priority Data

Jun. 1, 1995 [JP] Japan ................... 7-158499

[51] Int. Cl.$^6$ .................................................. A61M 16/00
[52] U.S. Cl. ................... 128/203.15; 128/203.12; 128/203.19; 128/203.21; 604/58
[58] Field of Search .................. 128/203.12, 203.15, 128/203.19, 203.21, 203.23; 604/58; 222/636; 141/18, 21, 330

[56] References Cited

U.S. PATENT DOCUMENTS

| | | | |
|---|---|---|---|
| 3,918,451 | 11/1975 | Steil | 128/203.15 |
| 5,048,514 | 9/1991 | Ramelle | 128/203.15 |
| 5,379,763 | 1/1995 | Mastin | 128/203.15 |

FOREIGN PATENT DOCUMENTS 1725415  4/1992  U.S.S.R. ................... 604/58

Primary Examiner—Vincent Millin
Assistant Examiner—V. Srivastava
Attorney, Agent, or Firm—Foley & Lardner

[57] ABSTRACT

An inhaler type medicine administering device comprises a generally cylindrical inhaling piece including a holder accommodating section located at one side of the inhaling piece, and an inhaling mouth located at the other side of the inhaling piece. A generally cylindrical capsule holder is disposed in the holder accommodating section and formed with a capsule accommodating hole which opens at one end of the capsule holder. A capsule is to be disposed in the capsule accommodating hole. First and second pin insertion holes are formed in the capsule holder and the inhaling piece and respectively located to be connected with axially opposite sections of the capsule accommodating hole. Each pin insertion hole extends generally in a diametrical direction of the inhaling piece and the capsule holder. An air flow passage is axially formed at at least one of an inner peripheral surface of the inhaling piece and an outer peripheral surface of the capsule holder. The first and second pin insertion holes are communicated with each other through the air flow passage. Additionally, a perforator is provided having first and second pins which are to be inserted respectively into the first and second pin insertion holes to form holes in the capsule which holes are in communication with the air flow passage.

7 Claims, 7 Drawing Sheets

# MEDICINE ADMINISTERING INHALING DEVICE

BACKGROUND OF THE INVENTION

1. Field of the Invention

This invention relates to improvements in an inhaler type medicine administering device suitable for, for example, administering granular medicine into the lungs of a patient as the patient takes breaths.

2. Description of Related Art

In general, administering medicine into the lungs of an asthma patient or the like is carried out, for example, by injecting the medicine into the patient in two ways. The patient may inhale the medicine by using a liquid aerosol sprayer, or, where granular medicine is contained in a capsule, the patient may inhale the fine, granular medicine (having a grain size, for example, ranging from 5 to 10 mm) when the capsule breaks.

The capsule method of administering medicine is extensively employed because of readiness. This capsule method is usually accomplished as follows: The asthma patient holds an inhaler in hand and installs the capsule containing the granular medicine into the inhaler. Then, the patient breaks the capsule by making a hole in the capsule with a needle and holds an inhaling mouth of the inhaler in his or her mouth and takes breaths. As a result, the granular medicine is released through the broken holes of the capsule and sucked into the lungs of the patient.

However, difficulties have arisen with inhalers used in the above conventional medicine administering manner. The inhaler is adapted to form only one or two holes in the capsule so that the shape of the hole is nonuniform, thereby making it impossible to securely and sufficiently inhale the medicine. Additionally, a large amount of the granular medicine is unavoidably left in the capsule even after breathing-in action of the patient because of the broken shape or the opening area of the hole formed in the capsule. As a result, a predetermined amount of the medicine cannot be administered to the patient.

Furthermore, with the conventional inhaler, the granular medicine tends to adhere to the inner surface of the inhaling mouth. This not only lowers the medicine administering efficiency but also requires frequent cleaning of the inhaling mouth. Additionally, it is difficult to eject the empty capsule out of the inhaler after administration of the medicine. It takes a relatively long time to eject the capsule. Accordingly, the time the patient touches the inhaling mouth of the device or the like is prolonged, which is not desirable from a sanitary viewpoint.

SUMMARY OF THE INVENTION

It is an object of the present invention to provide an improved inhaler type medicine administering device which can overcome drawbacks encountered in conventional inhalers for administering medicine to patients.

Another object of the present invention is to provide an improved inhaler type medicine administering device of relatively small size by which medicine stored in a capsule can be effectively administered to a patient.

A further object of the present invention is to provide an improved inhaler type medicine administering device having a capsule holder with a relatively small diameter by which almost all of the medicine stored in a capsule can be administered to the lungs of a patient.

An inhaler type medicine administering device of the present invention comprises a generally cylindrical inhaling piece including a holder accommodating section located at a first side of the inhaling piece, and an inhaling mouth located at a second side of the inhaling piece. The second side is axially opposite the first side. A generally cylindrical capsule holder is disposed in the holder accommodating section and has a capsule accommodating hole which opens at a first end of the capsule holder. A capsule may be disposed in the capsule accommodating hole. First and second pin insertion holes are formed in the capsule holder and the inhaling piece and are respectively located to connect with axially opposite sections of the capsule accommodating hole. Each pin insertion hole extends generally in a diametrical direction of the inhaling piece and the capsule holder. An air flow passage is axially formed at at least one of an inner peripheral surface of the inhaling piece and an outer peripheral surface of the capsule holder. The first and second pin insertion holes communicate with each other through the air flow passage. Additionally, a perforator is provided having first and second pins which are to be inserted respectively into the first and second pin insertion holes to form holes in the capsule. The holes in the capsule communicate with the air flow passage.

In the above described inhaler type medicine administering device, a capsule first is fit into the capsule accommodating hole of the main body of the medicine administering device. Then, holes are formed in the capsule by the perforator. In this state, the patient breathes through the inhaling mouth so that the medicine within the capsule can be securely sucked into the lungs of the patient through the air flow passage and the inhaling mouth. Additionally, the air flow passage is formed at at least one of the inner peripheral surface of the holder accommodating section and the outer peripheral surface of the capsule holder, and therefore the inhaler type medicine administering device may be of a small size as compared with a device in which the air flow passage is axially formed in a solid section of the capsule holder.

BRIEF DESCRIPTION OF THE DRAWINGS

In the drawings, like reference numerals designate like parts and elements throughout the figures, in which.

DETAILED DESCRIPTION OF THE INVENTION

Figure 1:
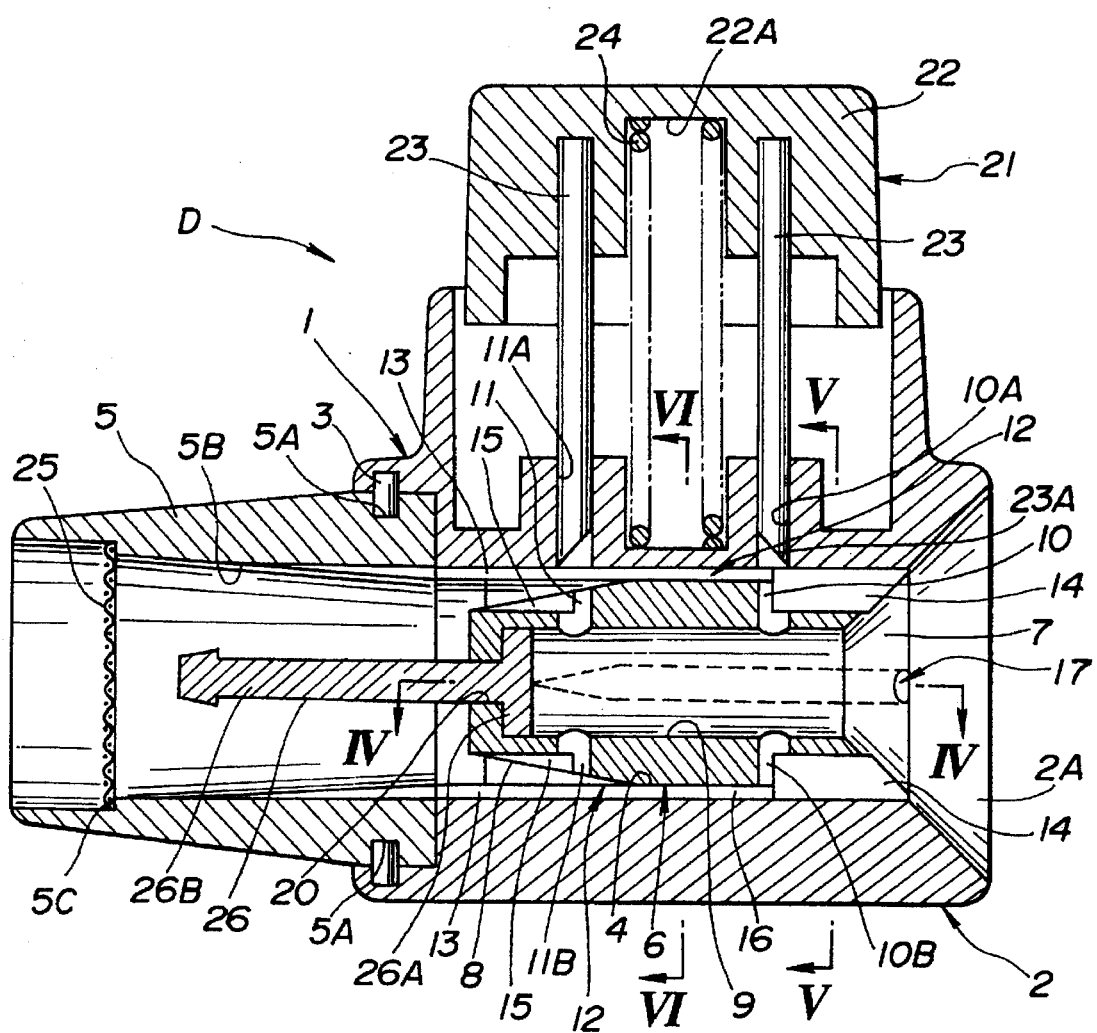
FIG. 1 is a vertical sectional view of an embodiment of an inhaler type medicine administering device in accordance with the present invention.
Figure 2:
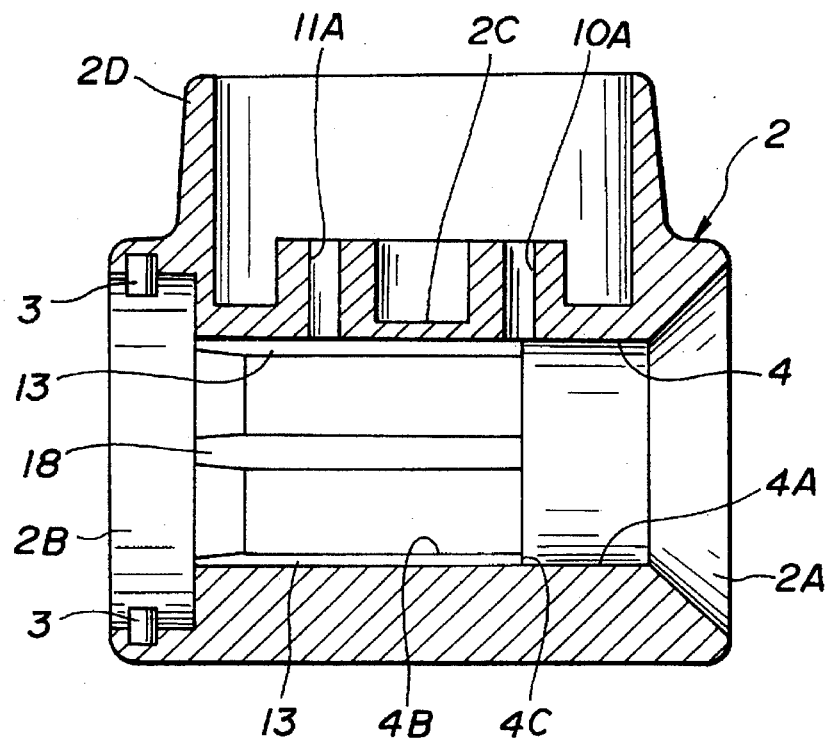
FIG. 2 is a vertical sectional view of a capsule accommodating section of an inhaling piece of the medicine administering device of FIG. 1.

Referring now to FIGS. 1 to 7 of the drawings, an embodiment of an inhaler type medicine administering device according to the present invention is illustrated by the reference character D. The medicine administering device D comprises an inhaling piece or main body 1 and an inhaling mouth 5. The inhaling piece 1 includes a holder accommodating section 2 located at one (first) side of the inhaling piece 1. As shown in FIG. 2, the holder accommodating section 2 is formed at its one (first) end section with an outer suction-side depression or hole 2A which has an annular surface. The annular surface tapers toward the other (second) end section opposite the first end section. The holder accommodating section 2 has an insertion hole 2B formed at the second end section. The one (first) end section of the inhaler mouth 5 may be inserted into the insertion hole 2B. The insertion hole 2B is defined by a generally cylindrical wall (not numbered) forming part of the holder accommodating section 2. This cylindrical wall is provided with two engaging pins 3 which are located opposite each other and project radially inwardly or into the insertion hole 2B.

Additionally, the holder accommodating section 2 has a central depression 2C formed at its outer peripheral section. The central depression 2C is located between outer pin insertion holes 10A and 11A which will be discussed below. A guide cylinder section 2D is formed in the outer peripheral section of the holder accommodating section 2 and located to surround the outer pin insertion holes 10A and 11A. The guide cylinder section 2D projects radially outwardly of the holder accommodating section 2 in such a manner that a support section 22 of a perforator 21 (discussed below) is movably disposed inside the guide cylinder section 2D.

The holder accommodating section 2 is formed with an axial holder insertion hole 4 which extends from the suction-side depression 2A to the insertion hole 2B. The holder insertion hole 4 includes a large diameter section 4A continuous with the suction-side depression 2A, and a small diameter section 4B continuous with the insertion hole 2B. The large diameter section 4A is adapted to receive therein a large diameter section 6A of a capsule holder 6 (discussed below), while the small diameter section 4B is adapted to receive therein a small diameter section 6B of the capsule holder 6. An annular step section 4C is formed between the cylindrical surfaces of the respective large and small diameter sections 4A and 4B so that the large diameter section 6A of the capsule holder 6, when brought into contact with the annular step section 4C, locates the capsule holder 6 within the holder insertion hole 4.

Figure 3:
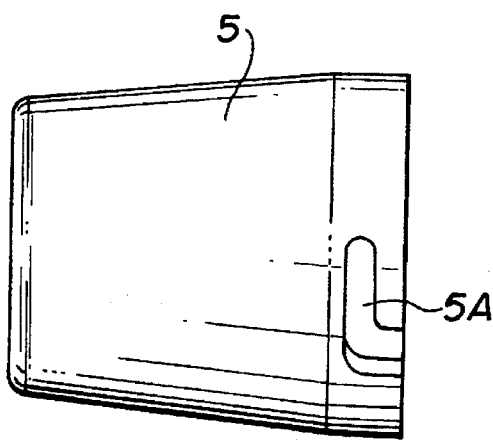
FIG. 3 is a front view of an inhaling mouth of the inhaling piece of FIG. 1.
Figure 4:
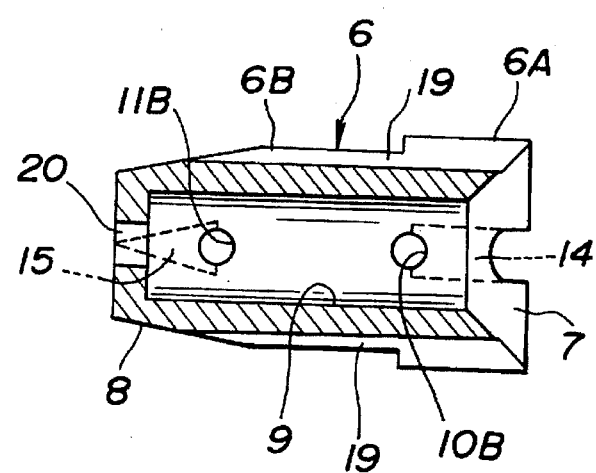
FIG. 4 is a cross-sectional view taken in the direction of arrows along line IV—IV of FIG. 1.

The inhaling mouth 5 is generally cylindrical and is disposed at the second end section of the holder accommodating section 2 in such a manner that its one (first) end section is detachably inserted in the insertion hole 2B of the holder accommodating section 2. The inhaling mouth 5 has a generally L-shaped engaging groove 5A formed at its outer peripheral surface, as shown in FIG. 3. The groove 5A can engage with, and disengage from, each engaging pin 3 by turning the inhaling mouth 5 around its axis relative to the holder accommodating section 2. The inside surface 5B of the inhaling mouth 5 is tapered toward the first end section of the inhaling mouth 5 or toward the small diameter section 4B of the holder insertion hole 4 of the holder accommodating section 2. In other words, the inside surface 5B is generally cylindrical to define a bore and has a diameter which increases in a direction toward the other (second) end section of the inhaling mouth 5 or in an opposite direction of the holder accommodating section 2 so that the medicine passing through the bore of the inhaling mouth 5 is dispersed toward the second or free end section of the inhaling mouth 5. Accordingly, the inside surface 5B is also referred to as a dispersion tapered surface. The bore defined by the inside surface 5B is smoothly continuous with the small diameter section 4B of the holder insertion hole 4. A step section 5C is formed at the inside surface 5B and located near the second end section of the inhaling mouth 5, and a broken piece trapping net 25 (discussed below) is fixed to the step section 5C.

The capsule holder 6 is inserted or tightly fitted within the holder insertion hole 4 of the holder accommodating section 2. The capsule holder 6 is generally cylindrical and has a large diameter section 6A located at its one (first) end side, and a small diameter section 6B located at the other (second) end side. The capsule holder 6 is located in position in such a manner that the large diameter section 6A is brought into contact with the annular step section 4C of the holder insertion hole 4. The large diameter section 6A has an inner suction-side depression 7 formed at its one (first) end. The inner suction-side depression 7 has an annular surface tapered toward the other (second) end (opposite the first end) of the large diameter section 6A or toward the small diameter section 6B. The small diameter section 6B has a surface (outflow-side tapered surface) 8 formed at its outer peripheral section. The surface 8 tapers toward the second end of the small diameter section 6B. The surface 8 is located at the second end section of the small diameter section 6B.

Figure 7:
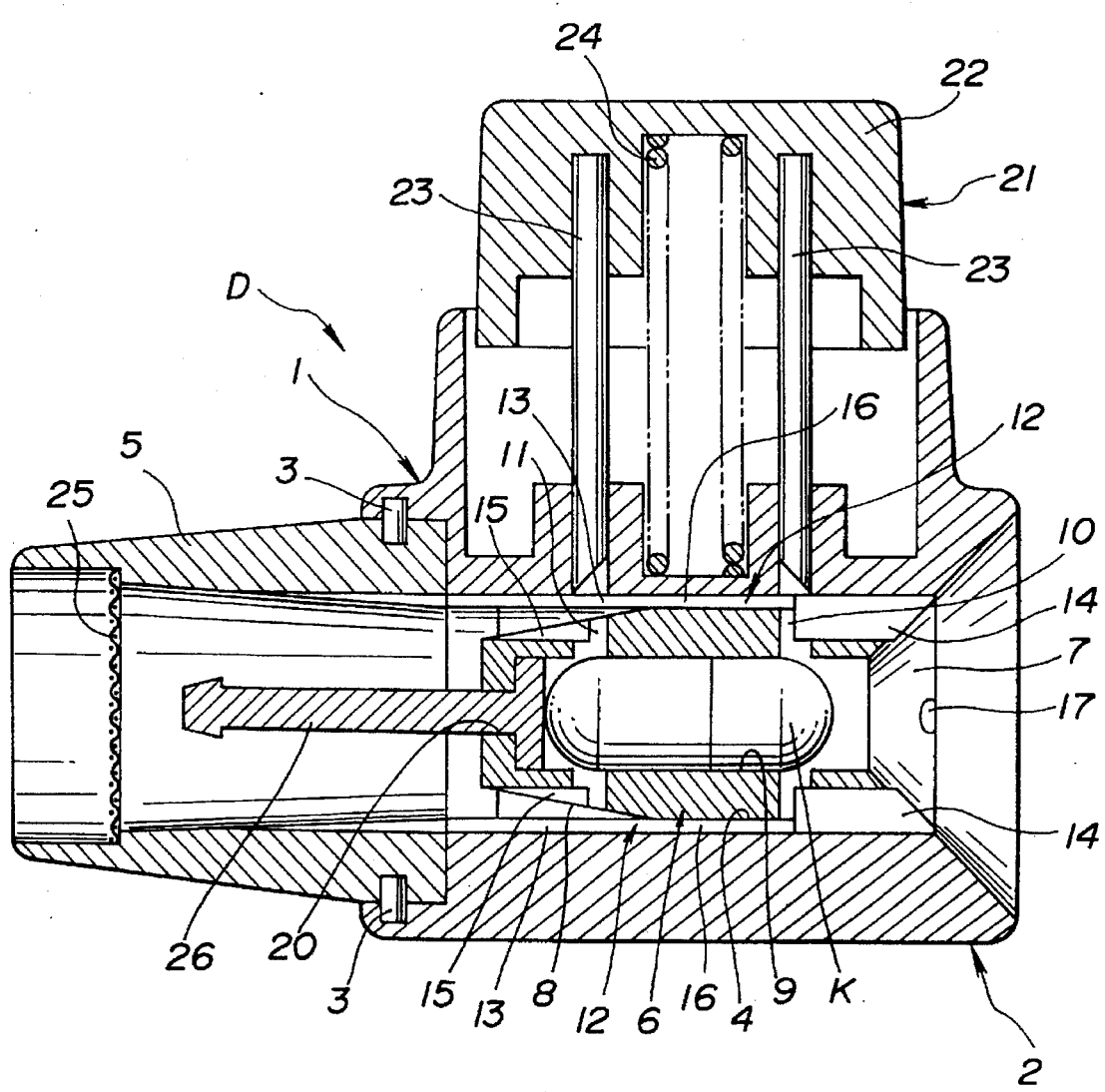
FIG. 7 is a vertical sectional view similar to FIG. 1 but showing a state in which a capsule is stored within a capsule accommodating hole of the holder accommodating section.

The capsule holder 6 is formed with an axially extending capsule accommodating hole 9 which is located coaxial with the capsule holder 6 and continuous at its one (first) end section with the suction-side depression 7. As shown in FIG. 7, a capsule K is to be inserted through the depression 7 into the capsule accommodating hole 9 so as to fit within the hole 9. The capsule K in this embodiment is formed generally into the shape of an elongate cylinder with hemispherically-shaped opposite ends, as shown in FIG. 7. Granular medicine is filled inside the capsule K.

The reference numeral 10 designates an inflow-side pin insertion hole which is located at one (first) end side of the capsule accommodating hole 9 and which diametrically extends through the holder accommodating section 2 and the capsule holder 6. The reference numeral 11 designates an outflow-side pin insertion hole which is located at the other (second) end side (opposite to the first end side) of the capsule accommodating hole 9 and which extends parallel to the inflow-side pin insertion hole 10. The pin insertion hole 10 includes an outside pin insertion hole 10A formed in the holder accommodating section 2, and an inside pin insertion hole 10B which diametrically passes through the capsule holder 6 and the capsule accommodating hole 9. The outside and inside pin insertion holes 10A and 10B are aligned with each other and communicate with each other. Similarly, the pin insertion hole 11 includes an outside pin insertion hole 11A formed in the holder accommodating section 2, and an outside pin insertion hole 11B which diametrically passes through the capsule holder 6 and the capsule accommodating hole 9. The outside and inside pin insertion holes 11A and 11b are aligned with each other and communicate with each other.

Figure 6:
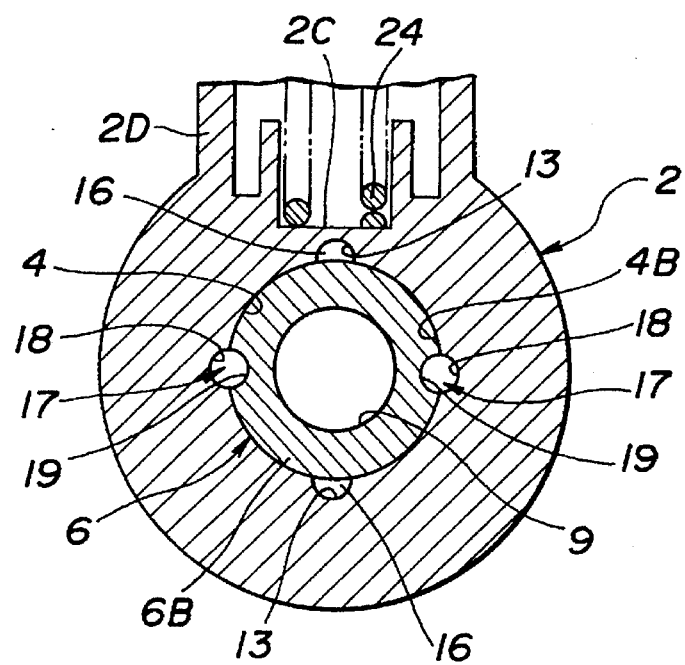
FIG. 6 is a cross-sectional view taken in the direction of arrows along line VI—VI of FIG. 1.

Two axial air flow passages 12 are formed through the inner peripheral surface of the inhaling piece 1 and the outer peripheral surface of the capsule holder 6 in such a manner as to communicate with the pin insertion holes 10 and 11. Each air flow passage 12 includes an outer groove 13, an inflow-side groove 14, and an outflow-side groove 15. The outer groove 13 is formed at the inner peripheral surface of the inhaling piece 1 to axially extend from the small diameter section 4B of the holder insertion hole 4 to the tapered surface 5B of the inhaling mouth 5. The inflow-side groove 14 is formed at the outer peripheral section of the large diameter section 6A of the capsule holder 6 to face to the outer groove 13. The inflow-side groove 14 is formed by cutting out a part of the large diameter section 6A extending from the inflow-side pin insertion hole 10 to the inner suction-side groove 7. The outflow-side groove 15 is formed at the small diameter section 6B of the capsule holder 6. The outflow-side groove 15 is formed by cutting out a part of the second end section of the small diameter section 6B through the outflow-side tapered surface 8. The cut-out part for the outflow-side groove 15 extends from the outflow-side pin insertion hole 11 to the second end of the capsule holder 6. As shown in FIG. 6, only a part of the outer groove 13 located between the inflow-side groove 14 and the outflow-side groove 15 serves as an orifice passage 16 for increasing the amount of air flow through the inside of the inhaling mouth 5 during inhaling of the medicine.

Each air flow passage 12 functions as follows: When a patient breathes in, air flows in through the inflow-side groove 14 and then is distributed into the inside pin insertion hole 10B and the orifice passage 16. Air flowing in the inside pin insertion hole 10B stirs the medicine in the capsule K and flows through the inside pin insertion hole 11B to be ejected together with the medicine through the outflow-side groove 15. At this time, air flows to be ejected through the orifice passage 16 necessarily generates an air flow which contains the medicine and passes from the outflow-side of inside pin insertion hole 11B to the outflow-side groove 15.

Figure 5:
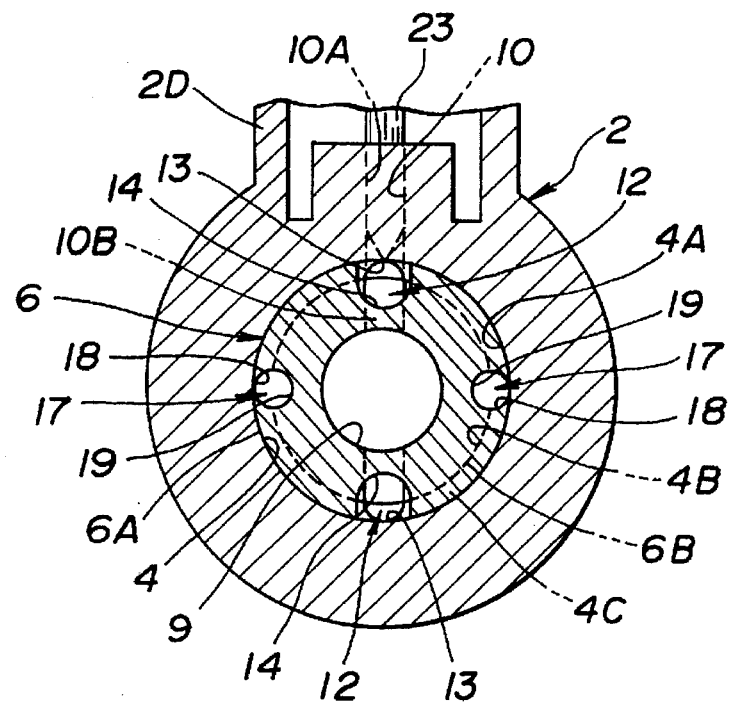
FIG. 5 is a cross-sectional view taken in the direction of arrows along line V—V of FIG. 1.

Two auxiliary air flow passages 17 are axially formed through the inner peripheral section of the inhaling piece 1 and the outer peripheral section of the capsule holder 6. Each auxiliary air flow passage 17 is positioned separate from each pin insertion hole 10 and 11 by an angle of 90 degrees in a peripheral direction, as seen in FIG. 5. Each auxiliary air flow passage 17 includes an outside groove 18 and an inside groove 19. The outside groove 18 is formed at the inner peripheral section of the inhaler piece 1 to axially extend from the small diameter section 4B of the holder insertion hole 4 to the dispersion tapered surface 5B. The inside groove 19 is formed at the outer peripheral section of the capsule holder 6 to face the outer groove 18. Each auxiliary air flow passage 17 functions to increase the amount of air flow when the patient breathes in through the inhaling mouth 5, thereby facilitating the patient's breathing-in action.

The capsule holder 6 is axially formed at the other (second) end with a through-hole 20 which communicates with the capsule accommodating hole 9. A capsule ejector 26, as discussed below, has an ejecting rod 26B which is to be inserted in the throughhole 20.

The perforator 21 is provided to form holes in the capsule K accommodated in the capsule accommodating hole 9, and includes the support section 22 which is movably disposed inside the guide cylinder section 2D of the holder accommodating section 2. The perforator 21 further includes two pins 23 which are fixedly supported at their base end section to the support section 22. The two pins 23 are arranged coaxially with the pin insertion holes 10 and 11 respectively. Each pin 23 has a free end section formed in the shape of a sharp needle 23A. The support section 22 is formed with a depression 22A which faces the depression 2C of the holder accommodating section 2. A return or compression spring 24 is located between the holder accommodating section 2 and the support section 22 of the perforator 21 and has opposite end sections which are respectively disposed in the depressions 2C and 22A. The return spring 24 functions to return the support section 22 and the pins 23 to their initial position after forming holes in the capsule K, where the sharp needle 23A of each pin 23 is located in the outside pin insertion hole 10A and 11A.

Figure 8:
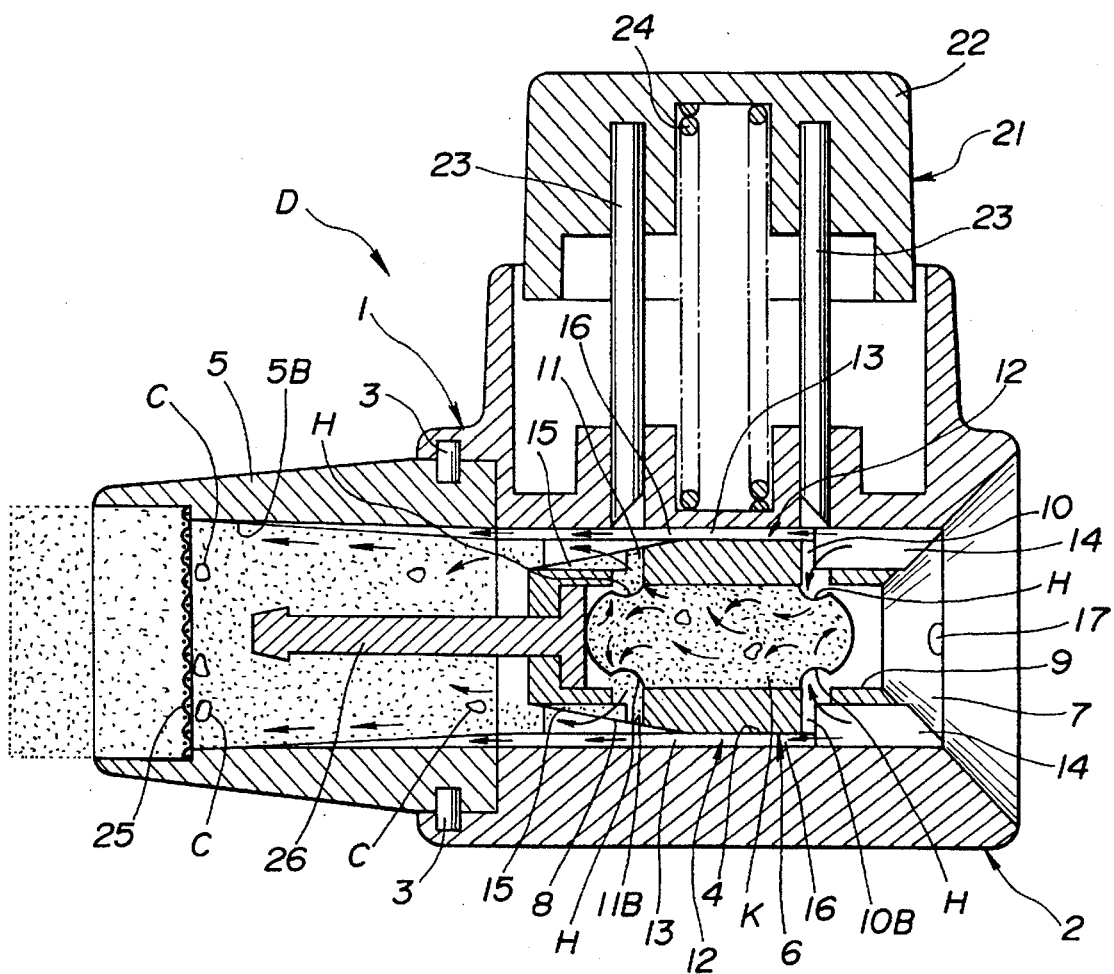
FIG. 8 is a vertical sectional view similar to FIG. 1 but showing a flowing state of air and medicine from the capsule when air is sucked by a patient.

The perforator 21 functions as follows: The support section 22 of the perforator 21 is pushed into the guide cylinder section 2D against the bias of the return spring 24 so that the pins 23 are inserted into the pin insertion holes 10 and 11, respectively. Accordingly, the sharp needles 23A of the pins 23 pass through the inside pin insertion holes 10B and 11B and then pass through the capsule K stored in the capsule accommodating hole 9 so that through-holes H, as shown in FIG. 8, are diametrically formed in the capsule K at axially opposite end sections of the capsule K. When a thrust force to push the support section 2D is removed, the support section 22 and the pins 23 are returned to the initial position under the bias of the return spring 24.

The broken piece trapping net 25 is disposed inside the inhaling mouth 5 and spreads throughout the bore of the inhaling mouth 5. The net 25 includes a wire-netting or mesh formed of fine wires, and the net 25 is disc-shaped. The peripheral section of the net 25 is located at and fixed to the step section 5C of the inhaling mouth 5 by means of bonding, welding, or the like. As shown in FIG. 8, the net 25 functions as follows: Broken pieces C of the capsule K are produced when the through-holes H are formed in the capsule K by the perforator 21. The broken pieces C are sucked together with the medicine toward the bore of the inhaling mouth 5, but are trapped by the net 25 so that only the medicine passes through the net 25, and is inhaled by the patient, when the patient breathes. Additionally, the granular medicine, which may coagulate, is dispersed upon striking the net 25 so that the medicine is well pulverized.

The capsule ejector 26 is disposed in the capsule holder 6 to eject the capsule K stored in the capsule accommodating hole 9. The capsule ejector 26 includes a generally disc-shaped pushing section 26A having a diameter which is slightly smaller than that of the capsule accommodating hole 9. The pushing section 26A is disposed within the capsule accommodating hole 9 and is axially movable to push the capsule K in the capsule accommodating hole 9. The ejecting rod 26B extends through the through-hole 20 of the capsule holder 6 and has a base end section which is integral with the pushing section 26A. The tip end section of the ejecting rod 26B extends toward the broken piece trapping net 25. The ejecting rod 26B is axially movable relative to the capsule holder 6.

Figure 9:
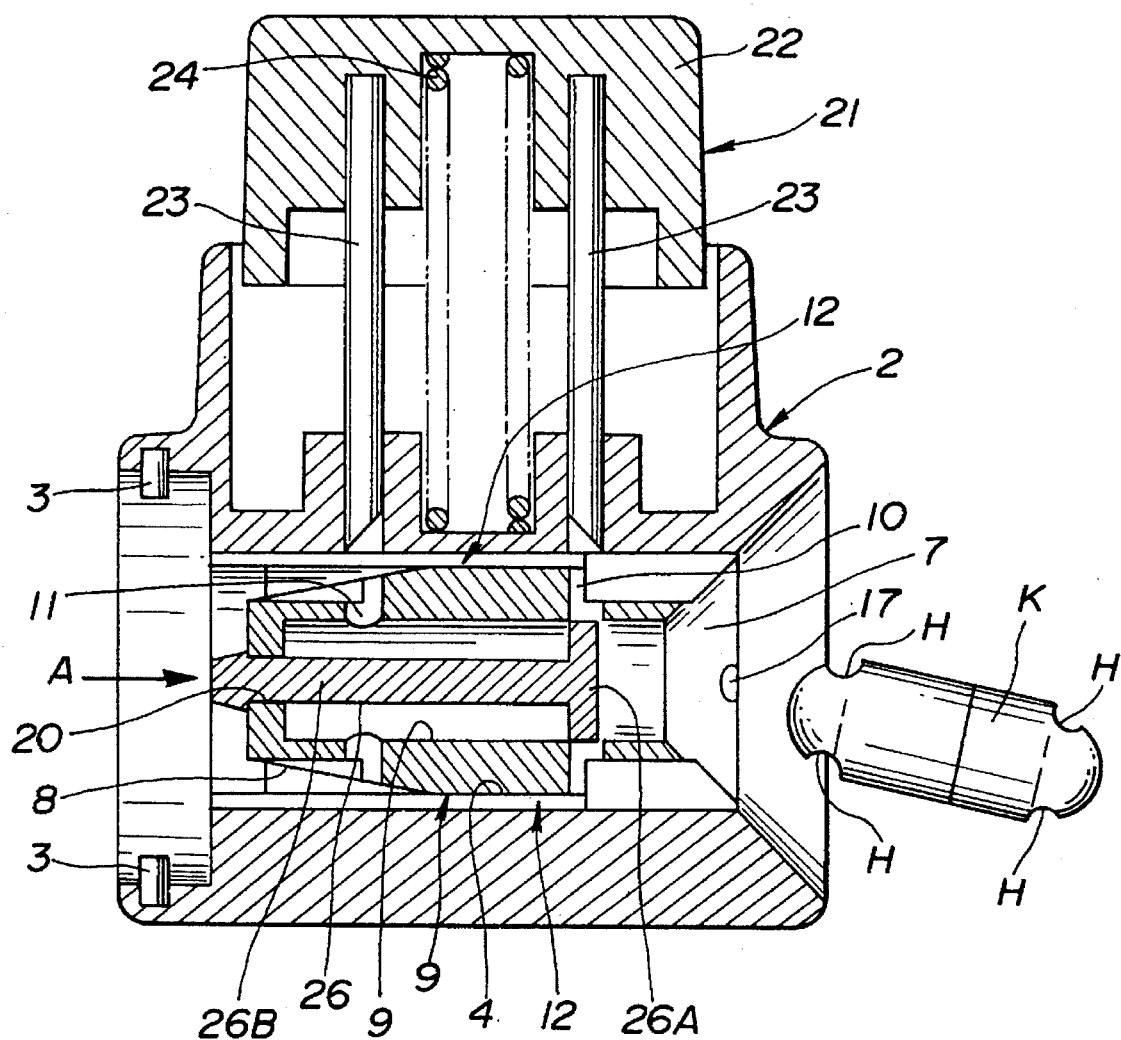
FIG. 9 is a vertical sectional view similar to FIG. 1 but showing a state in which the empty capsule has been ejected from the capsule accommodating hole under the action of a capsule ejector.

The capsule ejector 26 functions as follows: When administration of the medicine has been completed, the ejecting rod 26B of the capsule ejector 26 is pushed in a direction indicated by an arrow A by a fingertip or the like, as shown in FIG. 9, thereby pushing the empty capsule K out of the medicine administering device D. The capsule may then be discarded.

Next, a manner of operation of the above inhaler type medicine administering device D will be discussed with reference to FIGS. 8 and 9. First, preparation of the medicine administering device before the patient inhales the medicine will be discussed.

As shown in FIG. 1, the capsule holder 6 is first inserted into the holder insertion hole 4 of the holder accommodating section 2 through the one (first) end side so that the large diameter section 6A of the capsule holder 6 is fit with the annular step section 4C of the holder insertion hole 4. At this time, the outside pin insertion holes 10A and 11A formed in the holder accommodating section 2 are respectively brought into alignment with the inside pin insertion holes 10B and 11B, thereby forming the inflow-side pin insertion hole 10 and the outflow-side pin insertion hole 11. Each air flow passage 12 comprises the outer groove 13, the inflow-side groove 14 and the outflow-side groove 15, while each auxiliary air flow passage 17 comprises the outside groove 18 and the inside groove 19. The capsule holder 6 is pressfitted in the holder accommodating section 2 so as not to be usually detached.

Subsequently, in order for the patient to inhale the medicine, the capsule K is fit in the capsule accommodating hole 9 through the suction-side depression or hole 7 formed at the one (first) end of the capsule holder 6. It will be understood that the suction-side depression 7 is tapered and smoothly continuous with the tapered outer suction-side depression or hole 2A of the holder accommodating section 2, and therefore the capsule K can be easily guided into the capsule accommodating hole 9.

Then, when the capsule K has been stored in the capsule accommodating hole 9, the support section 22 of the perforator 21 is pushed along the guide cylinder section 2D so that the respective pins 23 are inserted into the pin insertion holes 10 and 11. As a result, four through-holes H are formed in the capsule K. After this hole formation action, the support section 22 and the respective pins 23 of the perforator 21 are returned to their initial position under the biasing force of the return spring 24.

Next, the flow of air and medicine within the inhaler type medicine administering device during inhaling of the medicine by the patient will be discussed, with reference to FIG. 8.

First, the inhaling mouth 5 is held in the patient's mouth. In this state, the patient breathes in, thereby generating air flow in directions indicated by the arrows in FIG. 8. Accordingly, air flows into the capsule accommodating hole 9 of the medicine administering device D through the inflow-side groove 14 and the inside pin insertion hole 10B of each air flow passage 12, and then flows into the capsule K through the through-holes H formed at the one (first) side of the capsule K. Air flowing into the capsule K necessarily disperses the granular medicine so that the medicine is mixed into air.

Air within the capsule K that now contains the medicine flows through the through-holes H formed at the other (second) side of the capsule K and through the inside pin insertion hole 11B and each outflow-side groove 15 to the side of the inhaling mouth 5.

Additionally, a part of the air sucked through each inflow-side groove 14 flows through each orifice passage 16, separately from the above-mentioned air flow, and is ejected through each outside groove 13 to the side of the inhaling mouth 5, thereby generating air flow (containing the medicine) from the outflow-side of inside pin insertion hole 11B to the outflow-side groove 15 under the action of air flowing and ejected through each orifice passage 16. As a result, air containing the medicine can be reached the lungs of the patient through the inside of the mouth and trachea of the patient, and the medicine is effectively administered into the lungs of the patient.

Furthermore, each air flow passage 12 and each auxiliary air flow passage 17 are formed through or at the inner peripheral surface of the inhaling piece 1 and the outer peripheral surface of the capsule holder 6. Therefore, air ejected through each air flow passage 12 and 17 flows along the dispersion tapered surface 5B of the inhaling piece 5, thereby blowing off any medicine adhered to the dispersion tapered surface 5B. Further, the dispersion tapered surface 5B gradually increases in diameter toward the other (second) end of the inhaling mouth 5 so that the medicine passing through the dispersion tapered surface 5B is released out of the inhaling mouth 5 in a dispersed state.

During inhaling, the broken pieces C produced when the respective through-holes H are formed, are not sucked together with the medicine into the lungs of the patient, but rather are trapped by the broken piece trapping net 25 so that only the medicine reaches the lungs of the patient. When the medicine strikes against the broken piece trapping net 25, it is well pulverized, thus preventing the medicine from dropping and staying in the medicine administering device D during inhaling the medicine so that the medicine can be securely supplied to the lungs of the patient.

Thereafter, when all of the medicine within the capsule K has been inhaled, the inhaling mouth 5 is detached from the holder accommodating section 2. Detaching the inhaling mouth 5 can be easily accomplished by holding and manually turning a part of the inhaling mouth 5 near the one (first) end. It will be understood that a part of the inhaling mouth 5 to be held in the patient's mouth is located axially opposite the part that may be manually turned and, therefore, can be protected from contamination by various germs.

Then, after the inhaling mouth 5 has been detached, the ejecting rod 26B of the ejector 26 projecting from the capsule holder 6 is pushed in a direction indicated by an arrow A in FIG. 9 in order to eject the empty capsule K out of the capsule accommodating hole 9. As a result, the capsule K within the capsule accommodating hole 9 can be easily ejected from the capsule accommodating hole 9 under the pushing action of the pushing section 26A.

As appreciated from the above description, according to the present invention, each air flow passage 12 and each auxiliary air flow passage 17 are formed through or at the inner peripheral surface of the inhaling piece 1 and the outer peripheral surface of the capsule holder 6. Therefore, the outer diameter of the capsule holder 6 can be reduced as compared with a device in which such air flow passages are formed axially only in the solid section of the capsule holder. The present medicine administering device thus is relatively small-sized. More specifically, each air flow passage 12 comprises the outer groove 13 formed at the inner peripheral surface of the inhaling piece 1, the inflow-side groove 14 formed at the outer peripheral surface of the capsule holder 6, and the outflowside groove 15 formed at the outer peripheral surface of the capsule holder, while each auxiliary air flow passage comprises the outside groove 18 formed at the inner peripheral surface of inhaler piece 1 and the inside groove 19 formed at the outer peripheral surface of the capsule holder 6. Therefore, the air flow passages 12 and 17 are formed through or at both the inner peripheral surface of the inhaling piece 1 and the outer peripheral surface of the capsule holder 6, so that the wall thickness of the inhaling piece 1 and the capsule holder 6 can be reduced, thereby further contributing to the small size of the present medical administering device.

Furthermore, air from each air flow passage 12 and from each auxiliary air flow passage 17 may flow along the dispersion tapered surface 5B of the inhaling mouth 5. Accordingly, any medicine adhered onto the dispersion tapered surface 5B may be securely removed by the air flowing along the dispersion tapered surface 5B. This reduces the frequency that the inhaling mouth 5 must be cleaned and allows a predetermined amount of the medicine to be administered to the patient, thereby improving the reliability of the medicine administering device.

Further, since the dispersion tapered surface 5B is configured to gradually increase in diameter toward the other (second) end of the inhaling mouth 5, or in a direction away from the holder accommodating section 2, the medicine passing through the dispersion tapered surface 5B is released out of the inhaling mouth 5 in a dispersed state. The medicine thus can be efficiently supplied to the lungs of the patient.

The broken pieces C of the capsule K are trapped by the broken piece trapping net 25 fixed at the inner peripheral portion of the inhaling mouth 5, and therefore the patient will not suffer a coughing fit from sucking the broken pieces together with the medicine into the trachea during inhaling of the medicine. Thus, only the medicine is inhaled by the patient, thereby improving the reliability of a medicine administering device of this type.

Since the inhaling mouth 5 is detachably connected to the holder accommodating section 2, the broken pieces trapped by the broken piece trapping net 25 can be easily discharged, thereby improving the operational efficiency of cleaning or the like. Additionally, if a plurality of the inhaling months 5 are carried by a plurality of patients, respectively, only one basic section comprising the capsule holder 6, the perforator 21, and the like may be commonly used by the patients, thereby reducing economical burden to the patients.

Besides, the empty capsule K can be easily and securely ejected from the capsule accommodating hole 9 of the capsule holder 6 by the capsule ejector 26 provided in the capsule holder 6, and therefore the operability of the medicine administering device is improved.

Figure 10:
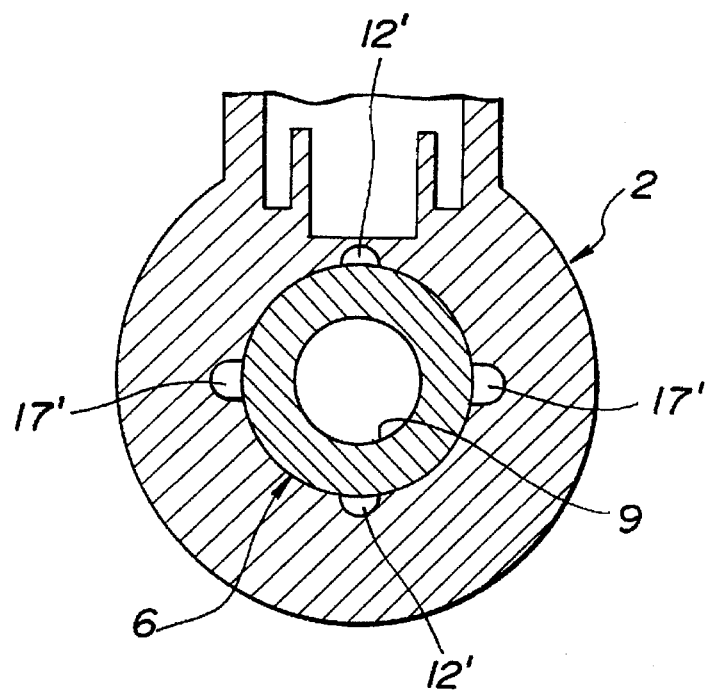
FIG. 10 is a cross-sectional view similar to FIG. 6 but showing a modified example of the embodiment of the inhaler type medicine administering device according to the present invention.
Figure 11:
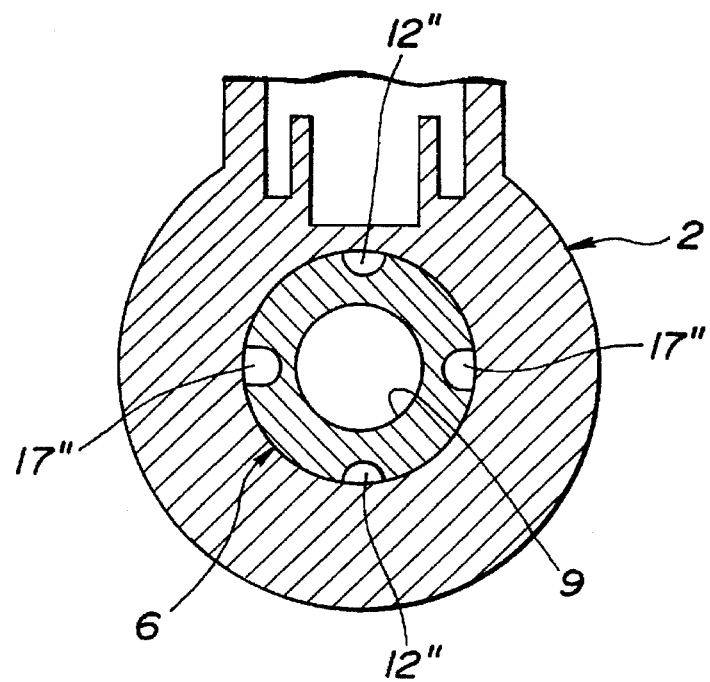
FIG. 11 is a cross-sectional view similar to FIG. 6 but showing another modified example of the embodiment of the inhaler type medicine administering device according to the present invention.

While each air flow passage 12 and each auxiliary air flow passage 17 have been shown and described as being formed through or at both the inner peripheral surface of the inhaling piece 1 and the outer peripheral surface of the capsule holder 6, it will be understood that each passage 12 and each passage 17 may be replaced with each air flow passage 12' and each auxiliary air flow passage 17', respectively, both of which are formed only at the inner peripheral surface of the holder accommodating section 2, as illustrated in FIG. 10. Otherwise, each passage 12 and each passage 17 may be replaced with each air flow passage 12" and each auxiliary air flow passage 17", respectively, both of which are formed only at the outer peripheral surface of the capsule holder 6, as illustrated in FIG. 11.

While the inhaling mouth 5 of the present medicine administering device has been shown and described as being detachably connected to the holder accommodating section 2 in such a manner that the engaging pins 3 of the holder accommodating section 2 are engageable with the engaging grooves 5A formed in the inhaling mouth 5, it will be understood that inhaling mouth 5 and the holder accommodating section 2 may be detachable from each other by means of fitting projections and depressions formed on them or by engaging threads (screws) formed on them.

Although the two air flow passages 12 and the two auxiliary air flow passages 17 have been shown and described as being formed in the present medicine administering device, it will be understood that the number of the air flow passages 12 and of the auxiliary air flow passages 17 may not be limited to two. The number may be decreased or increased to be, for example, one, four or the like, according to the patient's breathing-in force or the capacity of the patient's lungs. Additionally, each auxiliary air flow passage may be omitted if unnecessary.

What is claimed is:

1. A medicine administering device comprising:
    a generally cylindrical inhaling piece including a hold accommodating section located at a first side of said inhaling piece, and an inhaling mouth located at a second side of said inhaling piece, the second side being axially opposite to said first side;
    a generally cylindrical capsule holder disposed in said holder accommodating section and formed with a capsule accommodating hole which opens at a first end of said capsule holder, said capsule accommodating hole adapted for receipt of a capsule,
    means defining first and second pin insertion holes which are formed in said capsule holder and said inhaling piece and respectively located to be connected with axially opposite sections of said capsule accommodating hole, each pin insertion hole extending generally in a diametrical direction of said inhaling piece and said capsule holder;
    means defining an air flow passage which is axially formed at at least one of an inner peripheral surface of said inhaling piece and an outer peripheral surface of said capsule holder, said first and second pin insertion holes being communicated with each other through said air flow passage; and
    a perforator having first and second pins which are to be inserted respectively into said first and second pin insertion holes to form holes in the capsule which holes are in communication with said air flow passage.

2. A medicine administering device as claimed in claim 1, further comprising means for forming first and second air flow paths when air is sucked through said inhaling mouth;
    said first air flow path including said first pin insertion hole in said capsule holder, said air flow passage, said second pin insertion hole in said capsule holder, and an inside of said inhaling piece;
    said second air flow path including said first pin insertion hole, said air flow passage, and the inside of said inhaling mouth.

3. A medicine administering device as claimed in claim 1, wherein said air flow passage defining means includes means defining a first groove formed axially at the inner peripheral surface of said inhaling piece, and means defining a second groove formed axially at the outer peripheral surface of said capsule holder, said second groove facing said first groove.

4. A medicine administering device as claimed in claim 1, further comprising means defining an auxiliary air flow passage formed axially at at least one of the inner peripheral surface of said inhaling piece and the outer peripheral surface of said capsule holder, said auxiliary air flow passage being formed separate from said first and second pin insertion holes to generate air flow through said auxiliary air flow passage when air is sucked through said inhaling mouth.

5. A medicine administering device as claimed in claim 1, wherein said inhaling mouth has an inner peripheral surface which gradually increases in diameter in a direction away from said holder accommodating section.

6. A medicine administering device as claimed in claim 1, further comprising means by which said inhaling mouth is detachably attached to said holder accommodating section.

7. A medicine administering device as claimed in claim 1, further comprising a capsule ejector including an ejecting rod movably disposed in and extending through a through-hole formed at a second end of said capsule holder, and a capsule pushing section connected to said ejecting rod and located in the capsule accommodating hole.

* * * * *